(12) United States Patent
Thompson et al.

(10) Patent No.: US 8,491,958 B2
(45) Date of Patent: Jul. 23, 2013

(54) AVOIDANCE OF NON-SPECIFIC BINDING ON AN ACOUSTIC WAVE BIOSENSOR USING LINKER AND DILUENT MOLECULES FOR DEVICE SURFACE MODIFICATION

(75) Inventors: Michael Thompson, Toronto (CA); Sonia Sheikh, Willowdale (CA); Jack Chih-Chieh Sheng, Ajax (CA); Christophe Blaszykowski, Toronto (CA)

(73) Assignee: Econous Systems Inc., Toronto, Ontario (CA)

( * ) Notice: Subject to any disclaimer, the term of this patent is extended or adjusted under 35 U.S.C. 154(b) by 74 days.

(21) Appl. No.: 13/154,067

(22) Filed: Jun. 6, 2011

(65) Prior Publication Data

US 2011/0306771 A1    Dec. 15, 2011

Related U.S. Application Data

(60) Provisional application No. 61/353,383, filed on Jun. 10, 2010.

(51) Int. Cl.
*B05D 5/12* (2006.01)
*C07F 7/12* (2006.01)

(52) U.S. Cl.
USPC ........... 427/100; 548/110; 556/438; 556/437; 556/428

(58) Field of Classification Search
USPC ............ 548/110; 556/438, 437, 428; 427/100
See application file for complete search history.

(56) References Cited

U.S. PATENT DOCUMENTS

| 7,207,222 B2 | 4/2007 | Thompson et al. | |
| 7,500,379 B2* | 3/2009 | Hines | 73/24.06 |
| 2011/0136262 A1* | 6/2011 | Ragavan et al. | 436/518 |

OTHER PUBLICATIONS

Thermo Scientific Avidin-Biotin Technical Handbook downloaded Nov. 28, 2012.*
Collings et al., "Biosensors: Recent Advances", Rep. Prog. Phys.b May 1, 1997, pp. 1397-1445.
Sadik et al., "Environmental Biosensors for Organochlorines, Cyanobacterial Toxins and Endocrine Disrupting Chemicals", Biotechnol. Bioprocess Eng. 2000, pp. 407-412.
Yu et al., "Biosensors in Drug Discovery and Drug Analysis", Analytical Letters, 38, Accepted Jun. 1, 2005, pp. 1687-1701.
Gooding, "Biosensor Technology for Detecting Biological Warfare Agents: Recent Progress and Future Trends", Analytica Chimica Acta 559, Available online Jan. 24, 2006, pp. 137-151.
Rusmini et al., "Protein Immobilization Strategies for Protein Biochips", Biomacromolecules 2007, 8, Published on Web Apr. 20, 2007, pp. 1775-1789.
Kim et al, "Molecular Recognition and Specific Interactions for Biosensing Applications", Sensors, Oct. 23, 2008, pp. 6605-6641.
Vericat et al., Surface Characterization of Sulfur and Alkanethiol Self-Assembled Monolayers on Au(111), Journal of Physics Condensed Matter 18, Nov. 17, 2006, pp. R867-R900.
Shenhar et al., "Self-Assembly and Self-Organization", Introduction to Nanoscale and Technology, 2004, pp. 41-74.
Ulman, "Formation and Structure of Self-Assembled Monolayers", Chem. Rev. 1996, pp. 1533-1554.
Lee et al., "Electrophilic Siloxane-Based Self-Assembled Monolayers for Thiol-Mediated Anchoring of Peptides and Proteins", Langmuir, American Chemical Society, 1993, pp. 3009-3014.
Azioune et al., "TOF-SIMS Surface and Interface Characterization of the Immobilized Camel Antibody (cAb) onto SAMs-COOH/Au Substrates", Elsevier, Applied Surface Science, Available online Apr. 27, 2004, pp. 402-405.
Chrisey et al., "Covalent Attachment of Synthetic DNA to Self-Assembled Monolayer Films", Nucleic Acids Research, Oxford University Press, vol. 24, 1996, pp. 3031-3039.
Saoud et al., "Linker Immobilization of Protein and Oligonucleotide on Indium-Tin-Oxide for Detection of Probe-Target Interactions by Kelvin Physics", Analyst, 134, Mar. 14, 2009, pp. 835-837.
Wink et al., "Self-Assembled Monolayers for Biosensors", Analyst, vol. 122, Apr. 1997, pp. 43R-50R.
Chaki et al., "Self-Assembled Monolayers as a Tunalbe Platform for Biosensor Applications", Biosensors Bioelectronics, 2001, pp. 1-12.
Luderer et al., "Immobilization of Oligonucleotides for Biochemical Sensing by Self-Assembled Monolayers: Thio-Organic Bonding on Gold and Silanization on Silica Surfaces", Top. Curr. Chem., 260, Sep. 16, 2005, pp. 37-56.
Ferretti et al., "Self-Assembled Monolayers: A Versatile Tool for the Formulation of Bio-Surfaces", Trends in Analytical Chemistry, vol. 19, No. 9, 2000, pp. 530-540.
Guilbault et al., "Analytical Uses of Piezoelectric Crystals: A Review", C R C Critical Reviews in Analytical Chemistry, vol. 19, Issue 1, Feb. 18, 1988, pp. 1-28.
Deakin et al., "Electrochemical Applications of the Quartz Crystal Microbalance", Analytical Chemistry, vol. 61, No. 20, Oct. 15, 1989, pp. 1147A-1154A.
Sheikh et al., "Acoustic Wave-Based Detection in Bionalytical Chemistry: Competition for Surface Plasmon Resonance?", Analytical Letters, 41, Available online Nov. 6, 2008, pp. 2525-2538.
Gronewold, "Surface acoustic wave sensors in the Bioanalytical field: Recent Trends and Challenges" Analytica Chimica Acta 603, 2007, pp. 119-128.
Rickert et al., "Biosensors Based on Acoustic Wave Devices", In Sensors Update, vol. 5, 1999, pp. 105-139.
Cavic et al., "Acoustic Waves and the Study of Biochemical Macromolecules and Cells at the Sensor-Liquid Interface", The Analyst, 24, Jul. 12, 1999, pp. 1405-1420.

(Continued)

*Primary Examiner* — Yong Chu
(74) *Attorney, Agent, or Firm* — Kathleen E. Marsman; Borden Ladner Gervais LLP

(57) ABSTRACT

An acoustic wave biosensor comprising a surface of a mixed self-assembling monolayer for receiving a probe-biomolecule is described herein. The biosensor surface may comprise a piezoelectric quartz crystal,—for detection purposes with the electromagnetic piezoelectric acoustic sensor (EM-PAS)—upon which a mixed self-assembling monolayer is formed, which includes at least one linker, such as 2,2,2-trifluoroethyl-13-trichlorosilyl-tridecanoate (TTTA); its oligoethylene glycol (OEG) analog OEGylated TTTA (OEG-TTTA);   S-(2-(2-(2-(3-trichlorosilyl-propyloxy)-ethoxy)-ethoxy)-ethyl)-benzenethiosulfonate   (OEG-TUBTS). Linker/diluent systems for attaching a functionalizing entity to the surface of a biosensor are described, as well as methods for preparing a biosensor surface with an oligoethylene glycol linker.

18 Claims, 6 Drawing Sheets

OTHER PUBLICATIONS

Cooper et al., "A Survey of the 2001 to 2005 Quartz Crystal Microbalance Biosensor Literature: Applications of Acoustic Physics to the Analysis of Biomolecular Interactions", Journal of Molecular Recognition, 20, 2007, pp. 154-184.

Lange et al., "Surface Acoustic Wave Biosensors: A review", Anal Bional Chem, 391, Feb. 12, 2008, pp. 1509-1519.

Ballantyne et al., "Electromagnetic Excitation of High Frequency Acoustic Waves and Detection in the Liquid Phase", The Analyst, 2003, Jul. 7, 2003, pp. 1048-1055.

Thompson et al., "Superior Analytical Sensitivity of Electromagnetic Excitation Compared to Contact Electrode Instigation of Transverse acoustic", The Analyst, Feb. 2, 2004, pp. 219-224.

McGovern et al., "Self-Assembled Silanes and the Thiol Functionalization of Surfaces", Anal. Communication, 35, Oct. 27, 1998, pp. 391-393.

McGovern et al., "Thiol Functionalization of Surfaces for Biosensor Development", Can. J. Chem., vol. 77, 1999, pp. 1678-1689.

Wasserman et al., "Structure and Reactivity of Alkylsiloxane Monolayers Formed by Reaction of Alkyltrichlorosilanes on Silicon Substrates", Langmuir, vol. 5, No. 4, 1989, pp. 1074-1087.

Fryxell et al., "Nucleophilic Displacements in Mixed Self-Assembled Monolayers", Langmuir, vol. 12, No. 21, 1996, pp. 5064-5075.

Lee et al., "Characterization of a Self-Assembled Monolayer of Thiol on a Gold Surface and the Fabrication of a Biosensor Chip Based on Surface Plasmon Resonance for Detecting Anti-GAD Antibody", Biosensors and Bioelectronics 20, Available online Jun. 19, 2004, pp. 1422-1427.

Zheng et al., "Strong Repulsive Forces Between Protein and Oligo (Ethylene Glycol) Self-Assembled Monolayers: A Molecular Simulation Study", Biophysical Journal, vol. 89, Jul. 2005, pp. 158-166.

Ostuni et al., "A Survey of Structure—Property Relationships of Surfaces that Resist the Adsorption of Protein", Langmuir, vol. 17, No. 18, 2001, pp. 5605-5620.

Ngadi et al., "Are PEG Molecules a Universal Protein Repellent?", World Academy of Science, Engineering and Technology 49, 2009, pp. 144-148.

Snellings et al., "Protein Adhesion at Poly(ethylene glycol) Modified Surfaces", Advanced Materials, vol. 12, No. 24, Dec. 15, 2000, pp. 1959-1962.

Ostuni et al., "Self-Assembled Monolayers That Resist the Adsorption of Proteins and the Adhesion of Bacterial and Mammalian Cells", Langmuir, vol. 17, No. 20, 2001, pp. 6336-6343.

Xia et al., "Functionalized Poly(ethylene glycol)-Grafted Polysiloxane Monolayers for Control of Protein Binding", Langmuir, vol. 18, No. 8, 2002, pp. 3255-3262.

Jeon et al., "Protein-Surface Interactions in the Presence of Polyethylene Oxide", Journal of Colloid and Interface Science, vol. 142, No. 1, Mar. 1, 1991, pp. 149-158.

Parsons et al., "Organic Disulfides and Related Substances. XIV. Aspects of the Reaction of Thiolsulfonates with Thiols", Journal Org. Chem. Soc., Jan. 25, 1965, pp. 1923-1926.

Kice et al., "A Kinetic Study of the Reaction of Mercaptans with Phenyl Benzenethiolsulfinate and Benzenethiolsulfonate in Aqueous Dioxane", Journal of the American Chemical Society, May 30, 1974, pp. 8015-8019.

Delgado et al., "Ring-Closing Metathesis in the Synthesis of Large and Medium-Sized Oxacycles. Application to the Synthesis of Polyoxygenated Macrocycles", J. Org. Chem., 1999, pp. 4798-4816.

Doyle et al., "Selectivity in Reactions of Allyl Diazoacetates as a Function of Catalyst and Ring Size from γ-Lactones to Macrocyclic Lactones", J. Org. Chem., 65, 2000, pp. 8839-8847.

Corona et al., "Synthesis of a Biotin-Derived Alkyne for PD-Catalyzed Coupling Reactions", Organic Letters, vol. 8, No. 9, Mar. 31, 2006, pp. 1883-1886.

Delaluz et al., "Synthesis and Use of a Biotinylated 3-Azisophenothiazine to Photolabel Both Amino- and Carboxyl-Terminal Sites in Calmodulin", Bioconjugate Chem., 6, 1995, pp. 558-566.

Galonic et al., "Aziridine-carboxylic Acid-Containing Peptides: Application to Solution and Solid-Phase Convergent Site-Selective Peptide Modification", J. Am. Chem. Soc., 127, 2005, pp. 7359-7369.

Eggins, Chemical Sensors and Biosensors, vol. 3 of Analytical Techniques in the Sciences, 2002, pp. 1-273.

Anderson et al., "Robust Sensing Films for Pathogen Detection and Medical Diagnostics", Proceedings of SPIE, vol. 7167, Frontiers in Pathogen Detection, 2009.

Camarero, "New Developments for the Site-Specific Attachment of Protein to Surfaces", Biophysical Reviews and Letters, vol. 1, No. 1, 2006, pp. 1-28.

* cited by examiner

Scheme 1

Scheme 2

Scheme 3

Scheme 4

Scheme 5

Scheme 6

Scheme 7

AVOIDANCE OF NON-SPECIFIC BINDING ON AN ACOUSTIC WAVE BIOSENSOR USING LINKER AND DILUENT MOLECULES FOR DEVICE SURFACE MODIFICATION

CROSS REFERENCE TO RELATED APPLICATIONS

This application claims the benefit of and priority to U.S. Provisional Patent Application No. 61/353,383 filed Jun. 10, 2010, entitled: Avoidance of Non-specific Binding on an Acoustic Wave Biosensor Using Linker and Diluent Molecules for Device Surface Modification, the entirety of which is hereby incorporated by reference.

FIELD OF THE INVENTION

The present invention relates generally to acoustic wave biosensors implementing self-assembling monolayer chemistry and to the development of non-fouling molecular surfaces that resist non-specific adsorption for biosensor applications.

BACKGROUND OF THE INVENTION

Biosensors are analytical devices that are employed for the detection and transduction of biochemical interactions occurring at the sensor-liquid interface.[1] Although one-use structures are common, there is significant interest in devices that produce measurable signals in a real-time, ideally label-free manner. This type of detection technology constitutes a particularly attractive analytical tool that has received increasing attention over recent years with respect to environmental,[2] food,[3] and drug analysis,[4] detection aspects of biochemical warfare,[5] and clinical diagnostics.[6] However, before a biosensor can be implemented as a reliable, commercially viable diagnostic device, there are a number of requirements to be addressed. The attachment of the biosensing element to the transducer must be performed in a highly controlled fashion in terms of surface distribution and spatial orientation. Moreover, biological activity must be retained upon binding[7] in order for the target analyte to interact efficiently with the surface-attached biochemical probe. Further, the device should display both high specificity and sensitivity towards the target analyte and provide reliable and reproducible results, even in the presence of potentially interfering species. The undesired "non-specific adsorption" of adversary species (as opposed to the "specific adsorption" of the target analyte) has been a common and prevailing concern with respect to the analysis of complex biological samples such as blood, serum or urine. Accordingly, considerable attention has been paid to the role of adsorption effects and surface chemistry on biosensor response.

Self-assembling monolayer (SAM) chemistry is regularly regarded as a method of choice for the quick and economical preparation of structurally well-defined and customizable thin organic surfaces.[8] SAM chemistry relies on the use of linking molecules that are engineered to spontaneously form ordered molecular assemblies on solid inorganic substrates.[8] Moreover, functionalizable SAMs can also be designed to immobilize, in a subsequent step, various biomolecules such as proteins,[9] antibodies,[10] or oligonucleotides.[11] Understandably, these attractive properties have endowed SAM chemistry with a unique position for the fabrication of biosensors.[12]

The conversion of biological events into measurable signals requires the development of new transducing technologies that are capable of being interfaced with appropriate surface chemistry in an intimate overall structure. Amongst the various transducing systems and devices that have been engineered, those based on acoustic wave physics that commonly rely on the unique piezoelectric properties of quartz,[13,14] constitute an important, yet arguably underexploited[14] technology for application in the bioanalytical field.[15]

U.S. Pat. No. 7,207,222 entitled "Electromagnetic Piezoelectric Acoustic Sensor" describes a sensor that comprises a piezoelectric sensor plate spaced apart from an induced dynamic electromagnetic field, such as from an electromagnetic coil through which AC current flows. This acoustic wave device, referenced herein as EMPAS, is based on the electromagnetic excitation of higher harmonics in the piezoelectric substrate.[16] In practice, EMPAS offers several major advantages over its predecessors, such as an electrode-free environment and the ability to conduct measurements at tunable, ultra-high frequencies (up to 1.06 GHz), which allows for detailed information and enhances sensitivity.[17]

Following SAM formation, various biomolecules may be immobilized onto a sensor surface in a subsequent step[18] in order to formulate a functionalized surface for an intended application.

It is desirable to provide a biosensor having a functionalized surface that is capable of sensing a target analyte while minimizing non-specific adsorption of adversary species found in complex biological samples.

SUMMARY OF THE INVENTION

It is an object of the present invention to obviate or mitigate at least one disadvantage of previous biosensors.

Described herein is a novel biosensing technology that combines the electromagnetic piezoelectric acoustic sensor (EMPAS) technology and SAM chemistry, various surface linker and diluent molecules, and the method of preparation of such biosensors. Functionalizable mixed self-assembling monolayers (SAM) are described for use on a biosensor surface, onto which biomolecules can be subsequently immobilized in a straightforward and coupling-free manner. By preparing a functionalizable surface in this way, the development of EMPAS-based biosensors may be enhanced. The formation of novel, highly performing SAM-modified surfaces is described herein. These surfaces are applied to the real-time and label-free EMPAS detection of biotin-avidin interactions. Evaluation of the biosensing properties of sensors formed in this way is provided herein, in terms of specific and non-specific avidin adsorption.

The nature of the linking molecules described herein plays an important role on the overall performance of the sensor in terms of response to non-specific adsorption vs. specific interaction.

Described herein is an acoustic wave biosensor comprising a surface of a mixed self-assembling monolayer for receiving a biomolecule.

As further described herein there is provided oligoethylene glycol linkers for attaching a functionalizing entity to the surface of a biosensor and decrease the amount of non-specific adsorption.

Additionally, a method of preparing a biosensor surface comprising preparing the surface to receive a mixed self-assembling monolayer comprising an oligoethylene glycol (OEG) linker, and assembling the monolayer thereon, is described herein.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures.

DETAILED DESCRIPTION

Figure 1:
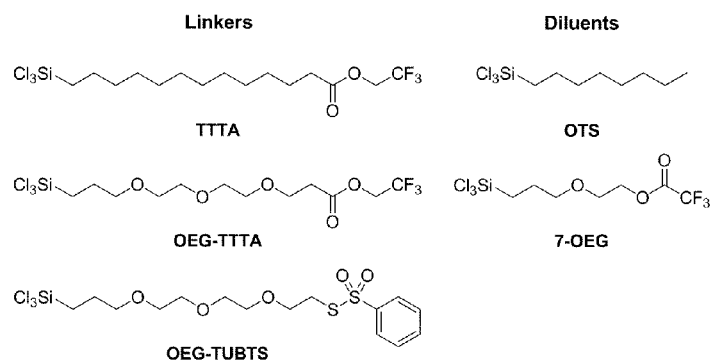
FIG. 1 illustrates schemes relevant to the Examples. Scheme 1 illustrates linker and diluent chemical structures, while Scheme 2 illustrates the formation of a mixed SAM onto a cleaned quartz crystal (step I) and the subsequent site-specific covalent immobilization of biotinthiol (step II): example with the TTTA/OTS linker/diluent system. OEG-TTTA/7-OEG and OEG-TUBTS/7-OEG systems follow the same scheme.
Figure 1:
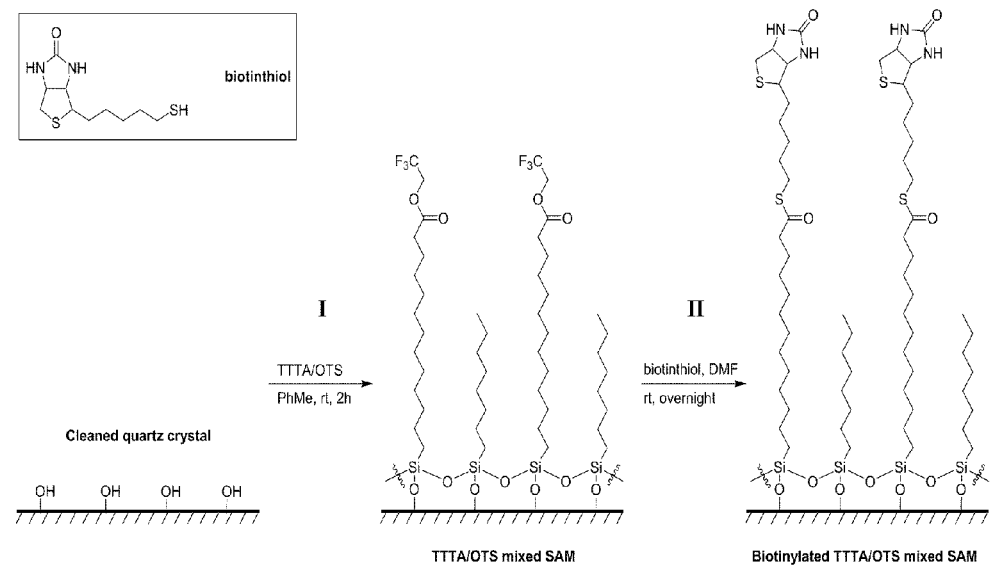

Generally, the present invention provides an acoustic wave biosensor comprising a surface of a mixed self-assembling monolayer for receiving a biomolecule. The biosensor surface comprises a piezoelectric quartz crystal surface with a mixed self-assembling monolayer (SAM). The mixed self-assembling monolayer can include 2,2,2-trifluoroethyl-13-trichlorosilyl-tridecanoate (TTTA); OEGylated TTTA (OEG-TTTA); S-(2-(2-(2-(3-trichlorosilyl-propyloxy)-ethoxy)-ethoxy)-ethyl)-benzenethiosulfonate (OEG-TUBTS) linker.

A linker/diluent system can be used in which the diluent may comprise octadecyltrichlorosilane (OTS) or 2-(3-trichlorosilyl-propyloxy)-ethyl-trifluoroacetate (7-OEG). Exemplary linker/diluent systems include TTTA/OTS, OEG-TTTA/7-OEG, or OEG-TUBTS/7-OEG.

The surface of the biosensor may be subsequently functionalized for analyte detection. Functionalization may involve a biotin derivative, such as biotinthiol.

Oligoethylene glycol linkers are described herein for attaching a functionalizing entity to the surface of a biosensor, for example OEG-TTTA/7-OEG, or OEG-TUBTS/7-OEG may be used.

A method for preparing a biosensor surface is described herein, which comprises preparing the surface to receive a self-assembling monolayer, followed by assembly of the monolayer thereon. Exemplary surfaces may include TTTA/OTS, OEG-TTTA/7-OEG, or OEG-TUBTS/7-OEG.

EXAMPLES

Exemplary embodiments of the invention are described below.

Example 1

OligoEthylene Glycol Linkers for the Surface Modification of an Ultra-High Frequency Acoustic Wave Biosensor The following exemplary embodiments describe the application of EMPAS acoustic wave technology for the real-time and label-free surface detection of biotin-avidin interactions. Biosensing surfaces are constructed onto unelectroded piezoelectric quartz discs as functionalizable mixed self-assembled monolayers (SAM) produced from previously unreported linker and diluent molecules. Biotinthiol can subsequently be immobilized for detection purposes in a straightforward and coupling-free manner. Specific and non-specific adsorptions of avidin are measured at tunable, ultra-high frequencies (1.06 and 0.82 GHz) with an electromagnetic piezoelectric acoustic sensor (EMPAS) using micromolar avidin-spiked buffer solutions. These biosensing surfaces, especially the oligoethylene glycol SAM-based variety, display high specificity for avidin, with moderate to excellent reproducibility. This work constitutes the first application of SAM chemistry and EMPAS technology in the bioanalytical field.

Methodology

The following includes detailed protocols for quartz disc cleaning, mixed SAM formation, biotinthiol immobilization and EMPAS measurements. Anhydrous toluene for SAM formation and freshly distilled anhydrous DMF (from $CaH_2$, under high vacuum) or spectrograde MeOH for biotinthiol immobilization were systematically used. Octadecyl-trichlorosilane (OTS) was distilled and stored in carefully sealed vials prior to use. $Et_3N$ was distilled from KOH. Avidin (from egg white, lyophilized powder) and Dulbecco's phosphate buffered saline (PBS) were purchased from Sigma-Aldrich®. Quartz crystals (AT-cut, 13.5 mm or 7 mm in diameter, 20 MHz fundamental frequency) were purchased from Lap-Tech Inc.®. Quartz crystal silanization (SAM formation) and biotinthiol immobilization reactions were prepared in a glovebox maintained under an inert ($N_2$) and anhydrous ($P_2O_5$) atmosphere. The crystals were systematically handled with thoroughly pre-cleaned stainless steel tweezers in order to minimize any external contamination. EMPAS measurements were performed at either 1.06 GHz (53rd harmonic) or 0.82 GHz (41st harmonic).

Avidin is well-known for exhibiting very high affinity towards biotin ($Ka \sim 10^{15}$ $M^{-1}$). This feature made the biotin-avidin system a valuable model for testing the viability of our biosensors. The interactive biotinyl residue was introduced onto the mixed SAMs upon immobilization of our probe-biomolecule, biotinthiol. For a comprehensive handbook on the biotin-avidin chemistry and its various applications in the bioanalytical field, see: Savage et al., 1992.[19]

Quartz Crystal Cleaning Procedure.

Quartz crystals (13.5 and 7 mm in diameter) were first sonicated in 20 mL of concentrated dishwashing soap for 30 minutes. The crystals were then thoroughly rinsed with hot water followed by distilled water then gently dried with forced air. Subsequently, the crystals were individually soaked in 6 mL of Piranha solution (3:1 (v/v) mixture of $H_2SO_4$ and 30% $H_2O_2$) pre-heated to 90° C. using a water bath (CAUTION: Piranha solutions are dangerous, and are to be handled with care). After 30 minutes, the crystals were rinsed with distilled water (3×) followed by spectrograde methanol (3×). Next, the crystals were sonicated in spectrograde methanol for 2 min then individually transferred into vials, which were subsequently placed in an oven maintained at 150° C. for drying. After 2 hours, the vials were immediately transferred into a humidity chamber, maintained at 60% relative humidity using a saturated solution of $MgNO_3 \cdot 6H_2O$, and set aside overnight.

Silanization Procedure (SAM Formation).

Neat linker (TTTA, OEG-TTTA or OEG-TUBTS, 10 μL) and neat diluent (OTS or 7-OEG, 10 μL) were separately diluted with anhydrous toluene (10 mL). 500 μL of each solution were mixed in individual test tubes into which cleaned quartz crystals were then soaked. The test tubes were sealed with rubber stoppers, removed from the glovebox, and placed on a spinning plate for 2 h. The crystals were then rinsed twice with dry toluene and finally sonicated in toluene for 5 minutes. After a final rinse with one portion of toluene, the previous procedure was repeated with dry chloroform. Finally, the crystals were rinsed twice with dry chloroform, gently dried under forced air then individually transferred into vials for storage (SAM characterization or EMPAS controls) or immediately engaged in the subsequent biotinthiol immobilization procedure (EMPAS samples).

Immobilization of Biotinthiol.

Biotinthiol solutions (1.0 mg/mL) for immobilization onto TTTA/OTS or OEG-TTTA/7-OEG mixed SAMs were prepared by dissolving biotinthiol into freshly distilled DMF. Biotinthiol solutions (1.0 mg/mL) for immobilization onto OEG-TUBTS/7-OEG mixed SAMs were prepared by dissolving biotinthiol into MeOH or a 1/1 (v/v) $MeOH/H_2O$ mixture, to which $Et_3N$ (1 μL per mL of solvent) was also added. These solutions were portioned (1 mL) in dry test tubes into which freshly prepared mixed SAM-coated quartz crystals were soaked. The test tubes were sealed with rubber stoppers, removed from the glovebox and placed on a spinning plate overnight. The crystals were then rinsed three times with spectrograde methanol, dried under a gentle $N_2$ stream then finally placed into screw cap vials under atmospheric conditions for EMPAS analysis.

EMPAS Measurements.

Avidin solutions (1.0 mg/mL) were prepared by dissolving 1.0 mg of solid avidin into 1 mL of PBS buffer. After the standard set-up of EMPAS,[17] biotinylated (or non-biotinylated) mixed SAM-coated quartz crystals were individually inserted into the flow through cell and PBS buffer was flown at a rate of 50 μL/min. Once the frequency signal stabilized, 50 μL of a freshly prepared 0.1 mg/mL avidin-spiked PBS solution (90 μL of PBS buffer+10 μL of 1.0 mg/mL avidin) were injected into the flow through system using a low-pressure chromatography valve. Once the avidin-spiked PBS solution completely passed over our surface, the uninterrupted PBS buffer flow rinsed the surface of any loosely bound material. The frequency signal stabilized again, the experiment was stopped and the frequency shift (for specific or non-specific avidin adsorption) was calculated.

Results and Discussion

The strategy first involved the preparation of robust and durable mixed SAMs onto hydroxylated AT-cut quartz discs using, in conjunction, combinations of unreported trichlorosilane linker and diluent molecules (FIG. 1, Scheme 1). Scheme 1 illustrates linker and diluent chemical structures. Both linkers and diluents possess a highly reactive trichlorosilyl tail function ($Cl_3Si$—), for strong and robust covalent anchorage onto the underlying hydroxylated quartz surfaces,[20] and an organic backbone to drive self-assembly and provide stability, rigidity and ordering to the mixed SAMs through intermolecular interactions.[8c] Linkers also possess reactive functionalizable head functions (trifluoroethyl ester (TFEE) or benzothiosulfonate (BTS)) for the subsequent site-specific covalent immobilization of a probe-biomolecule, biotinthiol (FIG. 1, Scheme 2), onto the mixed SAMs. Scheme 2 illustrates the formation of a mixed SAM onto a cleaned quartz crystal (step I) and the subsequent site-specific covalent immobilization of biotinthiol (step II): example with the TTTA/OTS linker/diluent system. OEG-TTTA/7-OEG and OEG-TUBTS/7-OEG systems follow the same scheme. Diluents are shorter molecules where the purpose is to space out linker molecules within otherwise inherently denser and congested "undiluted" assemblies.[21] This strategy decreases steric hindrance around neighboring linker head functional groups. As a result, mixed SAMs were anticipated to offer enhanced binding ability (better reactivity and accessibility) for biomolecule immobilization and to facilitate access with regard to target analyte binding.[7a, 9, 12a-c, 22]

Three types of mixed SAMs (TTTA/OTS, OEG-TTTA/7-OEG, and OEG-TUBTS/7-OEG) were successfully prepared upon immersion of cleaned quartz discs (13.5 or 7 mm in diameter) into the appropriate 1/1/2000 (v/v/v) linker/diluent solutions in anhydrous toluene, for 2 h at room temperature (FIG. 1, Scheme 2, step I). Mixed SAM characterization was achieved using contact angle goniometry (Table 1) and angle-resolved X-ray photoelectron spectroscopy (as outlined below in section entitled "Supporting Information"). These SAMs were then biotinylated in a single, straightforward, and coupling-free step, upon immersion into 1.0 mg/mL solutions of biotinthiol in anhydrous DMF or MeOH, overnight at room temperature (FIG. 1, Scheme 2, step II).

TABLE 1

Static contact angle measurements for TTTA/OTS, OEG-TTTA/7-OEG and OEG-TUBTS/7-OEG mixed SAMs recorded with ultrapure water

| Surface | Contact angle |
|---|---|
| TTTA/OTS SAM | 77° |
| OEG-TTTA/7-OEG SAM | 69° |
| OEG-TUBTS/7-OEG SAM | 75° |
| Cleaned quartz disc | 12° |

For each linker/diluent system, EMPAS experiments involved two sets of independent frequency shift measurements (4 to 6 replicates per set), that were conducted at 1.06 GHz (13.5 mm discs) or 0.82 GHz (7 mm discs) using 0.1 mg/mL solutions of avidin in phosphate buffer saline (PBS). On the one hand, biotinylated mixed SAMs (samples) were dedicated to record specific adsorption of avidin to biotin. On the other hand, non-biotinylated mixed SAMs constituted controls that were dedicated to quantify non-specific adsorption of avidin. Specific to non-specific adsorption frequency shift ratios ($R_{S/NS}$) and relative standard deviations (RSD) were then calculated to assess the efficiency of our biosensing surfaces to specifically detect avidin and the reproducibility of our measurements, respectively.

The TTTA/OTS system was first investigated on 13.5 mm discs (FIG. 2) which resulted in very encouraging results since the specific adsorption frequency shifts (15 kHz) were significantly larger than the ones recorded for non-specific adsorption (4 kHz). In each of the three pairings of bars shown in FIG. 2, the first of the two bars (lighter grey) is indicative of specific adsorption, whereas the second bar (darker grey) represents non-specific adsorption. For TTTA/OTS, $R_{S/NS}$ (13.5 mm discs)=3.8/1; for OEG-TTTA/7-OEG $R_{S/NS}$=6.3/1, and for OEG-TTA/7-OEG (7 mm discs) $R_{S/NS}$=4.1/1. The resulting $R_{S/NS}$ was excellent (3.8/1) and clearly demonstrating the ability of this system to detect avidin with high specificity. Reproducibility of measurements was reasonable for specific adsorption (RSD=14%). For non-specific adsorption, RSD=39%.

Figure 2:
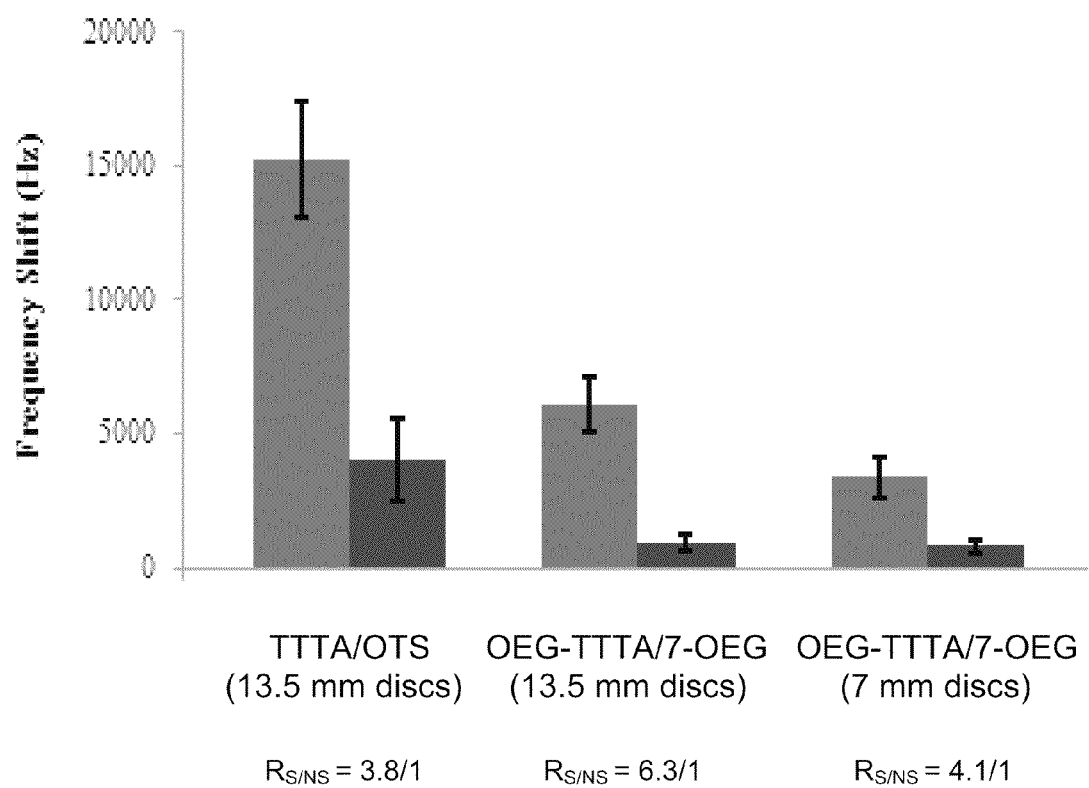
FIG. 2 illustrates EMPAS specific (light grey) and non-specific (dark grey) avidin adsorption frequency shifts respectively measured with biotinylated and non-biotinylated TTTA/OTS and OEG-TTTA/7-OEG mixed SAMs, using 0.1 mg/mL avidin-spiked PBS solutions. EMPAS measurements were recorded at 1.06 GHz for the 13.5 mm discs and at 0.82 GHz for the 7 mm discs.

In order to improve the performance of the system with respect to specific vs. non-specific adsorption, we next prepared OEG-TTTA/7-OEG mixed SAMs, TTTA/OTS mixed SAM analogs that possess oligoethylene glycol (OEG) backbones. This choice was motivated by the fact that OEGylated SAMs have been reported to act as non-fouling surfaces that successfully resist undesired non-specific adsorption,[23] a remarkable property that is currently drawing much attention in the bioanalytical field.[21,24] This approach is highly successful since OEG-TTTA/7-OEG mixed SAMs did indeed allow us to substantially improve the performance of our device (with a $R_{S/NS}$ now reaching 6.3/1), confirming the general observation that OEGylated SAMs exhibit non-fouling properties (FIG. 2, exp. 2). The reproducibility of the measurements for specific and non-specific adsorptions was found to be (RSD values) 16% and 33%, respectively. In view of the current trend towards biosensor miniaturization and in order to make our device even more attractive for future applications, next was prepared OEG-TTTA/7-OEG mixed SAMs on 7 mm discs—i.e. on surface areas four times smaller than those of the 13.5 mm discs (38 mm$^2$ vs. 142 mm$^2$). This new experiment (FIG. 2, exp. 3) was a success and provided an excellent yet slightly lower $R_{S/NS}$ of 4.1/1, indicating that our OEG-TTTA/7-OEG biosensing platforms could be considerably miniaturized while still maintaining high specificity for avidin. Reproducibility was shown to be RSD=23% for specific and RSD=33% for non-specific adsorptions.

As observed for the experimental results discussed above, the reproducibility of measurements constituted a limitation to our otherwise highly performing TFEE biosensing surfaces. It was hypothesized that low reproducibility values essentially reflect the fact that the biosensing surfaces of a same series, although prepared under identical conditions, likely display different linker/diluent compositions and distributions, surface morphologies, and/or biotinthiol loadings; i.e. discrepancies in binding affinity for avidin. In order to better control biotinthiol loadings, a new generation of linkers was next sought, which was able to reliably immobilize biotinthiol. Eventually OEG-TUBTS linker was synthesized (FIG. 1, Scheme 1), an OEGylated molecule that possesses a benzothiosulfonate (BTS) moiety known to readily and chemoselectively react with thiols to form disulfide bonds.[25] BTS functions also tolerate aqueous and alcoholic media,[25] which is particularly appreciable when probe-biomolecules are not soluble into aprotic organic solvents. It is also important to note that despite these remarkable properties, BTS-based molecules have never been involved within SAM chemistry or for the development of biosensors.

Figure 3:
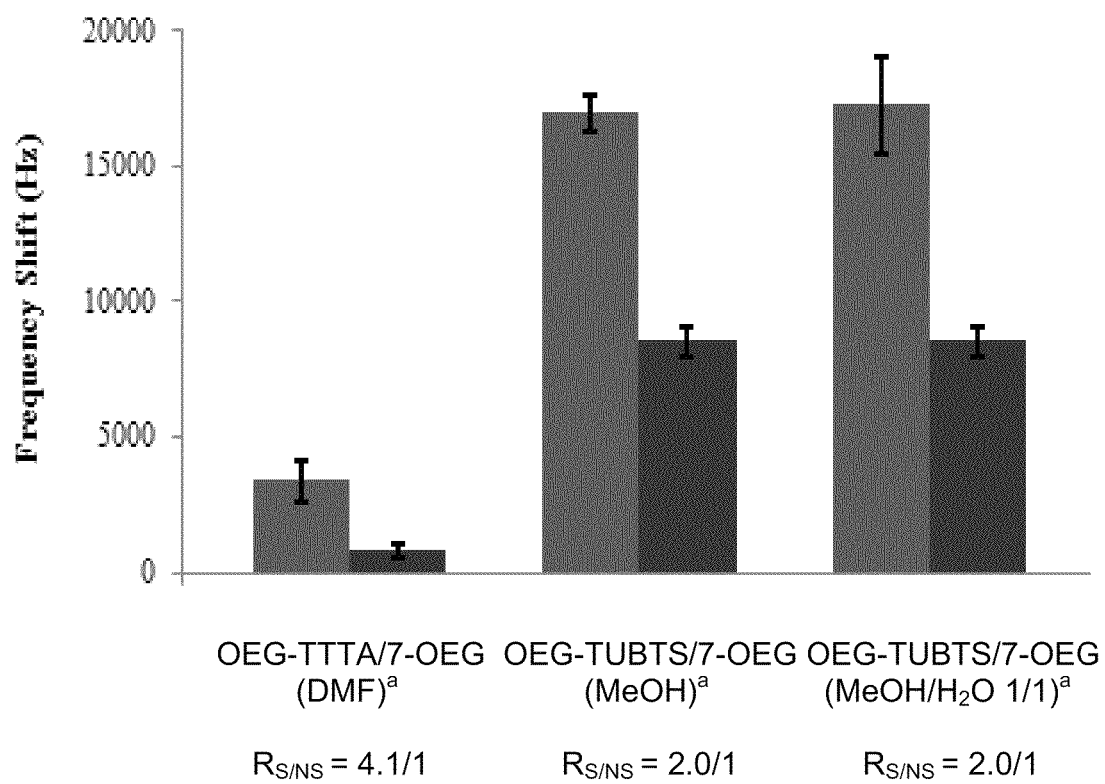
FIG. 3 illustrates EMPAS specific (light grey) and non-specific (dark grey) avidin adsorption frequency shifts respectively measured with biotinylated and non-biotinylated OEG-TUBTS/7-OEG mixed SAMs, using 0.1 mg/mL avidin-spiked PBS solutions, and comparison with the OEG-TTTA/7-OEG system. EMPAS measurements were recorded at 0.82 GHz on 7 mm discs.

FIG. 3 illustrates EMPAS specific (light grey) and non-specific (dark grey) avidin adsorption frequency shifts respectively measured with biotinylated and non-biotinylated OEG-TUBTS/7-OEG mixed SAMs, using 0.1 mg/mL avidin-spiked PBS solutions, and comparison with the OEG-TTTA/7-OEG system. EMPAS measurements were recorded at 0.82 GHz on 7 mm discs. Superscript $^a$ indicates solvent(s) used for biotinthiol immobilization. We first investigated OEG-TUBTS/7-OEG mixed SAMs (on 7 mm discs, at 0.82 GHz) for which biotinthiol had been immobilized in MeOH as the solvent (FIG. 3, exp. 2). These also exhibited the ability to detect avidin but with lower specificity ($R_{S/NS}$ of 2.0/1) compared to the corresponding TFEE SAMs (FIG. 3, exp. 1). Reproducibility was excellent, for both specific (RSD=4%) and non-specific (RSD=6%) adsorptions.

It is also interesting to note that, in comparison with the TFEE OEGylated mixed SAMs, both reproducibility and frequency shift intensities were considerably greater. For non-specific adsorption, this seems to indicate that BTS OEGylated mixed SAMs are more uniform and display comparatively higher affinity for avidin. With respect to specific adsorption, this strongly supports a higher, more reliably controlled and homogeneous site-specific biotinthiol coverage. Finally, it was necessary to determine whether specific adsorption is affected by immobilizing biotinthiol under mild aqueous conditions. For that purpose, we biotinylated OEG-TUBTS/7-OEG mixed SAMs in a 1/1 (v/v) MeOH/H$_2$O mixture (Biotinthiol is poorly soluble in water). It is noteworthy that neither the $R_{S/NS}$ (still 2.0/1) nor the RSD value for specific adsorption (10%) were significantly modified (FIG. 3, exp. 3), demonstrating that biotinthiol can also be reproducibly immobilized in an aqueous solvent mixture without altering the performance of the EMPAS biosensor.

Conclusion

This Example presents the construction of several novel, highly performing mixed SAM-based piezoelectric biosensors able to detect biotin-avidin interactions in a real-time and label-free manner using the electromagnetic piezoelectric acoustic sensor (EMPAS). This work constitutes the first application of SAM chemistry and EMPAS technology in the bioanalytical field. Biosensing surfaces were built onto piezoelectric AT-cut quartz discs as robust, durable and functionalizable mixed SAMs—using previously unreported trichlorosilane linker and diluent molecules—onto which biotinthiol could subsequently immobilize in a single, straightforward, and coupling-free step through TFEE or unprecedented BTS head functions. The biosensing properties of these assemblies, in terms of specific and non-specific avidin adsorptions, were measured with EMPAS at ultra-high frequencies (1.06 and 0.82 GHz) using micromolar avidin-spiked PBS buffer solutions. With respect to TFEE head function, biotinylated mixed SAMs efficaciously bound avidin, whereas non-biotinylated ones only exhibited limited binding affinities for avidin. Specific to non-specific avidin adsorption ratios were excellent and systematically improved with OEGylated mixed SAMs but the low reproducibility of our measurements was a recurrent problem. In comparison, BTS OEGylated mixed SAMs exhibited excellent reproducibility but lower specificity towards avidin. During this study, we also showed that the overall biosensing platform could be reduced in size while still maintaining high specificity for avidin (TFEE system) and that biotinthiol immobilization could also be performed under mild aqueous conditions without altering the performance of the sensor (BTS system). Research attention is currently focused on developing OEGylated mixed SAMs that would combine the high specificity displayed by TFEE systems and the excellent reproducibility obtained with BTS OEGylated mixed SAMs. It is also planned to progress from using simple buffered target analyte solutions to complex biological fluids such as serum, urine and blood in a real-world scenario. In these sample matrices, target analytes will be present at low concentration and will have to be distinguished from relatively high concentrations of competing species.

Supporting Information

General Remarks.

The following includes synthetic procedures and characterization data for linker, diluent and biotinthiol molecules as well as contact angle goniometry and X-ray photoelectron microscopy data for SAM characterization. $H_2PtCl_6 \cdot 6H_2O$ (99.9%) was purchased from Strem Chemicals Inc.®. Other chemicals were purchased from Sigma-Aldrich® and used as received unless otherwise noted. $^1H$ and $^{13}C$ NMR spectra were recorded at room temperature on Varian Mercury 300 or 400 MHz spectrometers using $CDCl_3$ or $CD_3OD$ as the NMR solvents. $^1H$ and $^{13}C$ NMR spectra are referenced to the residual solvent peak ($CDCl_3$: 7.27 ppm ($^1H$) and 77.23 ppm ($^{13}C$), $CD_3OD$: 3.31 ppm ($^1H$)).

TTTA Synthesis

Figure 4:
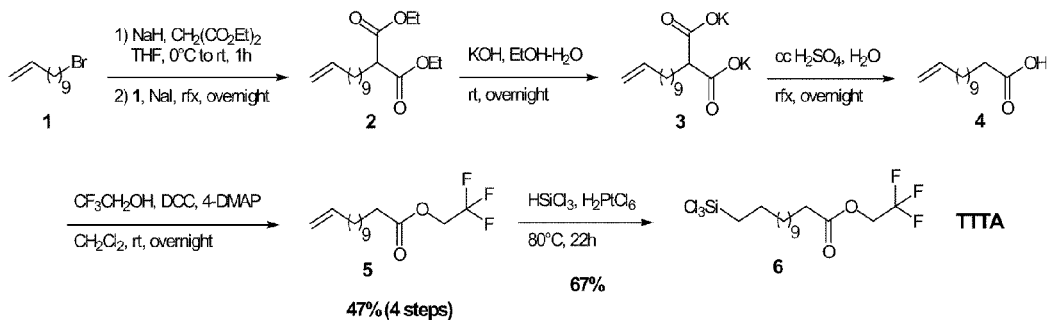
FIG. 4 illustrates Scheme 3, depicting TTTA synthesis.

FIG. 4 illustrates Scheme 3, depicting TTTA synthesis. TTTA (6) was synthesized in five steps from 11-bromo-undec-1-ene (1) with a 31% overall yield.

2,2,2-trifluoroethyl tridec-12-enoate (5)

To a stirred solution of NaH (60%, 484 mg, 12.1 mmol, 1.1 equiv.) in THF (50 mL) was added dropwise diethylmalonate (2.02 mL, 13.2 mmol, 1.2 equiv.) at 0° C. After addition, the reaction was allowed to warm to room temperature then stirred for 1 h. 11-bromo-undec-1-ene (1) (2.54 mL, 11.0 mmol, 1.0 equiv.) and anhydrous NaI (1.65 g, 11.0 mmol, 1.0 equiv.) were then successively added. After refluxing overnight, the reaction was quenched with brine then extracted with EtOAc. The combined organic layers were dried over anhydrous $Na_2SO_4$, filtered then evaporated under reduced pressure to provide crude diethyl malonate (2). The latter was diluted with a 1/1 (v/v) mixture of EtOH (20 mL) and 2.6 M KOH aqueous solution (20 mL). The reaction was vigorously stirred at room temperature overnight then the solvents were evaporated under reduced pressure to provide crude dipotassium malonate (3). The residue was then submitted to a $H_2O/CH_2Cl_2$ extraction. The combined aqueous layers were concentrated under reduced pressure to about 100 mL then carefully acidified with concentrated $H_2SO_4$. The reaction was refluxed overnight then submitted to a $CH_2Cl_2/H_2O$ extraction. The combined organic layers were dried over anhydrous $Na_2SO_4$, filtered then evaporated under reduced pressure to provide crude acid (4). The latter (2.06 g, 9.70 mmol, 1.0 equiv.) was dissolved in $CH_2Cl_2$ (70 mL) then DCC (2.22 g, 10.7 mmol, 1.1 equiv.), 2,2,2-trifluoroethanol (0.78 mL, 10.7 mmol, 1.1 equiv.) and 4-DMAP (0.12 g, 1.0 mmol, 0.1 equiv.) were successively added. The reaction was stirred at room temperature overnight then filtered through a short plug of Celite ($CH_2Cl_2$ washings). After evaporation of the filtrate under reduced pressure, the final purification was achieved by column chromatography on silica gel (Hexanes/EtOAc gradient) and provided 1.53 g (47%, 4 steps) of ester (5) as a pale yellow oil; $^1H$ NMR (400 MHz, $CDCl_3$) δ 5.81 (m, 1H), 4.99 (m, 1H), 4.93 (m, 1H), 4.47 (q, J=8.4 Hz, 2H), 2.41 (t, J=7.5 Hz, 2H), 2.04 (m, 2H), 1.64 (m, 2H), 1.32 (m, 14H); $^{13}C$ NMR (75 MHz, $CDCl_3$) δ 172.3, 139.4, 123.2 (q, J=275.5 Hz), 114.3, 60.3 (q, J=36.4 Hz), 34.0, 33.8, 29.8, 29.7, 29.6, 29.4, 29.3, 29.2, 29.1, 24.9; IR (neat) 1760 cm$^{-1}$; HRMS (EI, m/z) calcd. for $C_{15}H_{25}O_2F_3$ (M$^{+\bullet}$) 294.1807. found 294.1806.

2,2,2-Trifluoroethyl 13-Trichlorosilyl-TridecAnoate (TTTA) (6)

In a heavy-walled tube equipped with a magnetic stir bar, ester (5) (1.18 g, 4.00 mmol, 1.0 equiv.) and $H_2PtCl_6 \cdot 6H_2O$ (21 mg, 0.14 mmol, 1.0 mol. %) were loaded. The tube was transferred into a glovebox and $HSiCl_3$ (0.82 mL, 8.04 mmol, 2.0 equiv.) was added to the solution. The tube was tightly fastened then removed from the glovebox. The resulting solution was stirred at 80° C. for 22 h behind a protecting shield. Purification was achieved by Kugelrohr distillation under high vacuum and provided 1.16 g (67%) of TTTA (6) as a colorless oil; bp=170-180° C. (0.15 Torr); $^1H$ NMR (400 MHz, $CDCl_3$) δ 4.45 (q, J=8.5 Hz, 2H), 2.41 (t, J=7.4 Hz, 2H), 1.72-1.55 (m, 4H), 1.45-1.22 (m, 18H); $^{13}C$ NMR (100 MHz, $CDCl_3$) δ 172.4, 123.3 (q, J=275.8 Hz), 60.3 (q, J=36.4 Hz), 33.9, 32.0, 29.8, 29.7, 29.6, 29.5, 29.4, 29.2, 29.1, 24.9, 24.5, 22.5.

OEG-TTTA Synthesis

Figure 5:
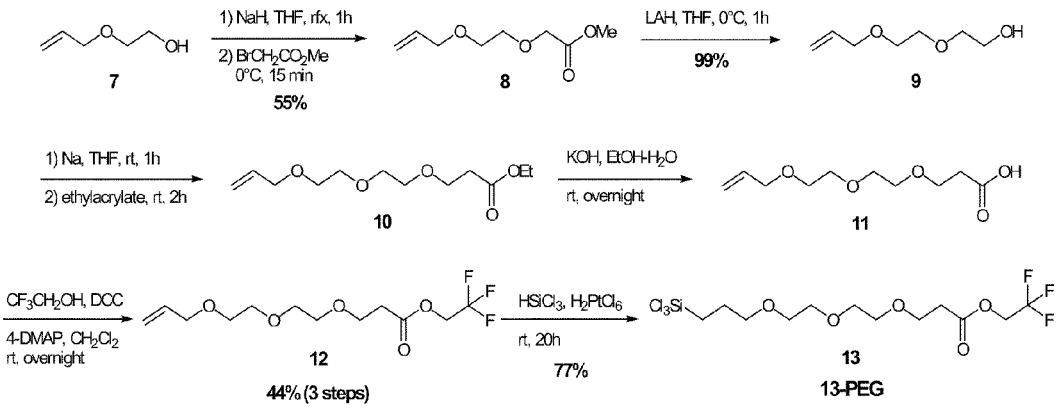
FIG. 5 illustrates Scheme 4, depicting OEG-TTTA synthesis.

FIG. 5 illustrates Scheme 4, depicting OEG-TTTA synthesis. OEG-TTTA (13) was synthesized in six steps from 2-allyloxy-ethanol (7) with a 18% overall yield.

Methyl (2-allyloxy-ethoxy)-acetate (8)

To a stirred solution of 2-allyloxy-ethanol 7 (10.9 mL, 100 mmol, 1.0 equiv.) in THF (200 mL) was carefully added NaH (60%, 4.8 g, 120 mmol, 1.2 equiv.) in small portions at room temperature. The reaction was then refluxed for 1 h (until $H_2$ release ceased) then cooled to 0° C. Methyl bromoacetate (11.4 mL, 120 mmol, 1.2 equiv.) was then added dropwise. After 15 min at 0° C., the reaction was submitted to a EtOAc/$H_2O$ extraction. The combined organic layers were washed with brine, dried over anhydrous $MgSO_4$, filtered then evaporated under reduced pressure. Purification was achieved by Kugelrohr distillation under reduced pressure and provided 9.77 g (55%) of ester (8) as a colorless oil; bp=130-145° C. (water tap vacuum); $^1H$ NMR (400 MHz, $CDCl_3$) δ 5.91 (m, 1H), 5.28 (m, 1H), 4.99 (m, 1H), 4.19 (s, 2H), 4.02 (m, 2H), 3.76 (s, 3H), 3.75 (m, 2H), 3.64 (m, 2H); $^{13}C$ NMR (100 MHz, $CDCl_3$) δ 171.1, 134.8, 117.3, 72.4, 71.2, 69.7, 68.9, 51.9; IR (neat) 1755 cm$^{-1}$; HRMS (ESI, m/z) calcd. for $C_8H_{15}O_4$ (MH$^+$) 175.0964. found 175.0960.

2-(2-allyloxy-ethoxy)-ethanol (9)

To a stirred solution of ester (8) (9.77 g, 55.1 mmol, 1.0 equiv.) in THF (100 mL) was carefully added one portion of LAH (95%, 1.10 g, 27.5 mmol, 0.5 equiv.) at 0° C. After 30 min, another portion of LAH was carefully added and the reaction was stirred for an additional 30 min. The reaction was then carefully quenched with a $Na_2SO_4$-saturated aqueous solution. The resulting white aluminum salts were then filtered off over a short plug of Celite (EtOAc washings) and the filtrate was evaporated under reduced pressure. Purification was achieved by Kugelrohr distillation under reduced pressure and provided 7.99 g (99%) of alcohol (9) as a colorless oil; bp>200° C. (water tap vacuum). Spectroscopic data were consistent with those reported in the literature.[26] $^1H$ NMR (400 MHz, $CDCl_3$) δ 5.92 (m, 1H), 5.28 (m, 1H), 5.19 (m, 1H), 4.04 (m, 2H), 3.73 (m, 2H), 3.68 (m, 2H), 3.62 (m, 4H), 2.36 (brs, 1H).

2,2,2-trifluoroethyl 3-(2-(2-allyloxy-ethoxy)-ethoxy)-propanoate (12)

To a stirred solution of alcohol (9) (8.77 g, 60.0 mmol, 2.2 equiv.) in THF (100 mL) was added freshly hexanes-degreased Na (0.2 g, 8.7 mmol, 0.3 equiv.) in small portions at room temperature. The reaction was then stirred at room temperature for 1 h (until the Na chunks disappeared). A solution of ethyl acrylate (2.97 mL, 27.3 mmol, 1.0 equiv.) in THF (30 mL) was then added dropwise (30 min) through an addition funnel. After 2 h at room temperature, the reaction was quenched with 10 drops of glacial acetic acid then submitted to a $CHCl_3/H_2O$ extraction. The combined organic layers were dried over anhydrous MgSO$_4$, filtered then evaporated under reduced pressure to provide crude ester (10). The latter was diluted with a 1/1 (v/v) mixture of MeOH (120 mL) and 2.5 M KOH aqueous solution (120 mL). The reaction was vigorously stirred at room temperature overnight then extracted with CHCl$_3$. The aqueous layer was carefully acidified with concentrated (38%) HCl then extracted with CHCl$_3$. The combined organic layers were dried over anhydrous MgSO$_4$, filtered then evaporated under reduced pressure to provide crude acid (11). The latter (4.05 g, 18.6 mmol, 1.0 equiv.) was diluted with CH$_2$Cl$_2$ (120 mL) then DCC (4.25 g, 20.4 mmol, 1.1 equiv.), 2,2,2-trifluoroethanol (1.50 mL, 20.4 mmol, 1.1 equiv.) and 4-DMAP (0.23 g, 1.9 mmol, 0.1 equiv.) were successively added. The reaction was stirred at room temperature overnight then filtered through a short plug of Celite (CH$_2$Cl$_2$ washings). After evaporation of the filtrate under reduced pressure, the final purification was achieved by column chromatography on silica gel (Hexanes/EtOAc gradient) and provided 3.59 g (44%, 3 steps) of ester (12) as a pale yellow oil; $^1$H NMR (400 MHz, CDCl$_3$) δ 5.92 (m, 1H), 5.28 (m, 1H), 5.18 (m, 1H), 4.40 (q, J=8.4 Hz, 2H), 4.03 (m, 2H), 3.79 (t, J=6.4 Hz, 2H), 3.63 (m, 8H), 2.71 (t, J=6.4 Hz, 2H); $^{13}$C NMR (100 MHz, CDCl$_3$) δ 170.2, 134.9, 123.1 (q, J=275.7 Hz), 117.2, 72.4, 70.9, 70.8, 70.7, 69.6, 66.3, 60.5 (q, J=36.5 Hz), 34.8; IR (neat) 1760 cm$^{-1}$; HRMS (ESI, m/z) calcd. for C$_{12}$H$_{20}$O$_5$F$_3$ (MH$^+$) 301.1257. found 301.1258.

2,2,2-trifluoroethyl 3-(2-(2-(3-trichlorosilyl-propyloxy)ethoxy)ethoxy)-propanoate 13 (OEG-TTTA)

In a heavy-walled tube equipped with a magnetic stir bar, ester (12) (1.65 g, 5.50 mmol, 1.0 equiv.) and H$_2$PtCl$_6$.6H$_2$O (28 mg, 0.06 mmol, 1.0 mol. %) were loaded. The tube was transferred into a glovebox and HSiCl$_3$ (1.12 mL, 11.00 mmol, 2.0 equiv.) was added to the solution. The tube was tightly fastened then removed from the glovebox. The resulting solution was stirred at room temperature for 20 h behind a protecting shield. Purification was achieved by Kugelrohr distillation under high vacuum and provided 1.85 g (77%) of OEG-TTTA (13) as a colourless oil; bp=175-185° C. (0.19 Torr); $^1$H NMR (400 MHz, CDCl$_3$) δ 4.47 (q, J=8.4 Hz, 2H), 3.78 (t, J=6.4 Hz, 2H), 3.61 (m, 8H), 3.51 (t, J=6.4 Hz, 2H), 2.70 (t, J=6.4 Hz, 2H), 1.85 (m, 2H), 1.48 (m, 2H); $^{13}$C NMR (100 MHz, CDCl$_3$) δ 170.1, 123.1 (q, J=275.7 Hz), 71.7, 70.8, 70.7, 70.6, 70.3, 66.3, 60.4 (q, J=36.6 Hz), 34.7, 22.7, 21.1.

OEG-TUBTS Synthesis

Figure 6:
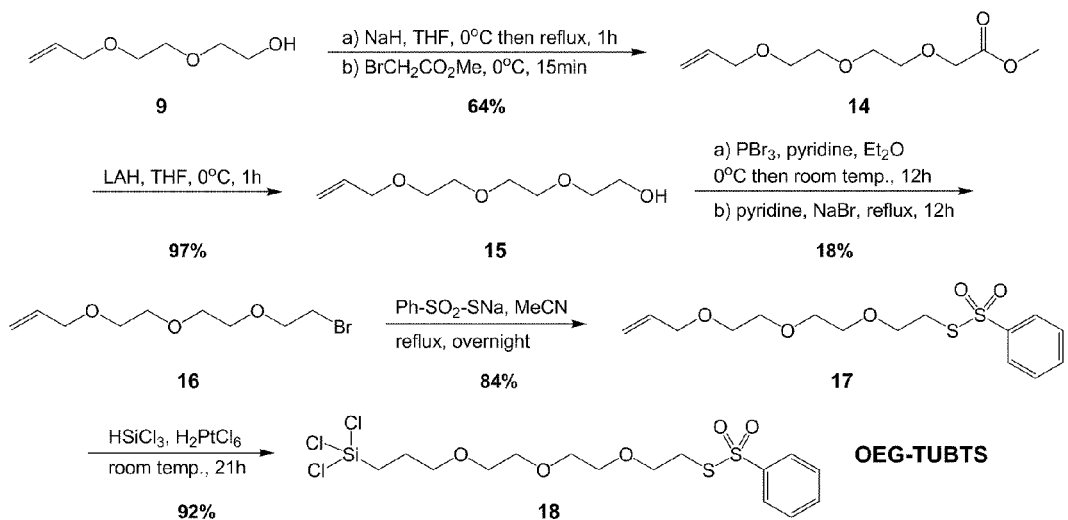
FIG. 6 illustrates Scheme 5, depicting OEG-TUBTS synthesis.

FIG. 6 illustrates Scheme 5, depicting OEG-TUBTS synthesis. OEG-TUBTS (18) was synthesized in five steps from alcohol (9) with a 9% overall yield.

Methyl (2-(2-allyloxy-ethoxy)-ethoxy)-acetate (14)

To a stirred solution of alcohol (9) (4.86 g, 33.2 mmol, 1.0 equiv.) in THF (70 mL) was carefully added NaH (60%, 1.60 g, 40.0 mmol, 1.2 equiv.) in small portions at room temperature. The reaction was then refluxed for 1 h (until H$_2$ release ceased) then cooled to 0° C. Methyl bromoacetate (3.8 mL, 40.1 mmol, 1.2 equiv.) was then added dropwise. After 15 min at 0° C., the reaction was submitted to a EtOAc/H$_2$O extraction. The combined organic phases were washed with brine, dried over anhydrous Na$_2$SO$_4$, filtered then evaporated under reduced pressure. Purification was achieved by distillation under high vacuum and provided 4.68 g (64%) of ester (14) as a colourless oil; bp=130-140 0° C. (0.09 Torr); $^1$H NMR (300 MHz, CDCl$_3$) δ 5.91 (m, 1H), 5.28 (m, 1H), 5.18 (m, 1H), 4.17 (s, 2H), 4.02 (m, 2H), 3.75 (s, 3H), 3.75-3.58 (m, 8H); $^{13}$C NMR (75 MHz, CDCl$_3$) δ 171.0, 134.8, 117.1, 72.3, 71.0, 70.8, 70.7, 69.5, 68.7, 51.8; IR (neat) 1754 cm$^{-1}$; HRMS (ESI, m/z) calcd. for C$_{10}$H$_{19}$O$_5$ (MH$^+$) 219.1236. found 219.1227.

2-(2-(2-allyloxy-ethoxy)-ethoxy)-ethanol (15)

To a stirred solution of ester (14) (4.60 g, 21.1 mmol, 1.0 equiv.) in THF (60 mL) was carefully added one portion of LAH (0.50 g, 12.5 mmol, 0.5 equiv.) at 0° C. After 30 min, another portion of LAH was carefully added and the reaction was stirred for an additional 30 min. The reaction was then carefully quenched with a Na$_2$SO$_4$-saturated aqueous solution. The resulting white aluminum salts were then filtered off over a short plug of Celite (EtOAc washings) and the filtrate was finally evaporated under reduced pressure to afford pure alcohol (15) (no purification required) as a pale yellow oil (3.89 g, 97%). Spectroscopic data were consistent with those reported in the literature:[26a] $^1$H NMR (400 MHz, CDCl$_3$) δ 5.93 (ddt, J=17.2, 10.3, 5.7 Hz, 1H), 5.28 (dq, J=17.2, 1.5 Hz, 1H), 5.19 (dq, J=10.3, 1.5 Hz, 1H), 4.04 (dt, J=5.7, 1.5 Hz, 2H), 3.78-3.58 (m, 12H); $^{13}$C NMR (75 MHz, CDCl$_3$) δ 134.8, 117.3, 72.7, 72.4, 70.8, 70.7, 70.5, 69.5, 61.8.

2-(2-(2-allyloxy-ethoxy)-ethoxy)-1-bromo-ethane (16)

To a stirred solution of alcohol (15) (3.83 g, 20.1 mmol, 1.0 equiv.) and pyridine (0.16 mL, 2.00 mmol, 0.1 equiv.) in Et$_2$O (20 mL) was added dropwise phosphorus tribromide (0.74 mL, 7.60 mmol, 0.36 equiv.) at 0° C. After 30 min, the reaction was allowed to warm to room temperature. As the reaction was not completed after 12 h, pyridine (1.60 mL, 20.0 mmol, 1.0 equiv.) and sodium bromide (4.14 g, 40.2 mmol, 2.0 equiv.) were successively added. After 12 h of reflux, the resulting solution was submitted to a EtOAc/NH$_4$Cl-saturated aqueous solution extraction. The combined organic phases were dried over anhydrous Na$_2$SO$_4$, filtered then evaporated under reduced pressure. Purification was achieved by column chromatography (Hexanes/EtOAc gradient) to afford bromide (16) (0.90 g, 18%) as a yellow oil; $^1$H NMR (300 MHz, CDCl$_3$) δ 5.93 (ddt, J=17.3, 10.5, 5.7 Hz, 1H), 5.28 (dq, J=17.3, 1.5 Hz, 1H), 5.19 (dq, J=10.5, 1.5 Hz, 1H), 4.03 (dt, J=5.7, 1.5 Hz, 2H), 3.82 (t, J=6.3 Hz, 2H), 3.71-3.65 (m, 6H), 3.64-3.59 (m, 2H), 3.48 (t, J=6.3 Hz, 2H); $^{13}$C NMR (75 MHz, CDCl$_3$) δ 134.9, 117.4, 72.5, 71.4, 70.9, 70.8, 70.7, 69.6, 30.5.

S-(2-(2-(2-allyloxy-ethoxy)-ethoxy)-ethyl)benzenethiosulfonate (17)

To a stirred solution of bromide (16) (0.90 g, 3.6 mmol, 1.0 equiv.) in MeCN (18 mL) was added benzenethionosulfonic acid sodium salt (85%, 1.64 g, 7.1 mmol, 2.0 equiv.) at room temperature. The reaction was refluxed overnight then submitted to a EtOAc/brine extraction. The combined organic phases were dried over anhydrous Na$_2$SO$_4$, filtered then evaporated under reduced pressure. Purification was achieved by column chromatography (Hexanes/EtOAc gradient) to afford benzenethiosulfonate (17) (1.04 g, 84%, >95% purity) as a pale yellow oil. An additional careful column chromatography afforded pure (17) as a pale yellow oil: $^1$H NMR (300 MHz, CDCl$_3$) δ 7.95 (m, 2H), 7.65 (m, 1H), 7.56 (m, 2H), 5.91 (m, 1H), 5.29 (m, 1H), 5.19 (m, 1H), 4.01 (m, 2H), 3.74-3.56 (m, 10H), 3.20 (t, J=6.3 Hz, 2H); $^{13}$C NMR (75 MHz, CDCl$_3$) δ 145.0, 134.9, 133.9, 129.5, 127.2, 117.3, 72.4, 70.8, 70.7, 70.6, 69.6, 69.2, 35.9; IR (neat) 3068, 1647, 1324, 1142 cm$^{-1}$; HRMS (ESI, m/z) calcd. for $C_{15}H_{23}S_2O_5$ (MH$^+$) 347.0971. found 347.0981.

S-(2-(2-(2-(3-trichlorosilyl-propyloxy)-ethoxy)-ethoxy)-ethyl)benzenethiosulfonate (18) (OEG-TUBTS)

In a heavy-walled tube equipped with a magnetic stirring bar, benzenethiosulfonate (17) (347 mg, 1.00 mmol, 1.0 equiv.) and $H_2PtCl_6.6H_2O$ (5.2 mg, 0.010 mmol, 1.0 mol. %) were loaded. The tube was transferred into a glovebox and HSiCl$_3$ (0.30 mL, 2.94 mmol, 3.0 equiv.) was added to the solution. The tube was tightly fastened then removed from the glovebox. The resulting solution was stirred at room temperature for 21 hours behind a protecting shield. HSiCl$_3$ excess was then removed under high vacuum to afford OEG-TUBTS (18) as a viscous yellow-orange cloudy oil (444 mg, 92%): $^1$H NMR (300 MHz, CDCl$_3$) δ 7.94 (m, 1H), 7.62 (m, 1H), 7.58 (m, 1H), 7.46 (m, 1H), 7.32 (m, 1H), 3.85-3.55 (m, 16H), 3.20 (t, J=6.2 Hz, 1H), 2.80 (t, J=6.2 Hz, 1H).

7-OEG Synthesis

Figure 7:
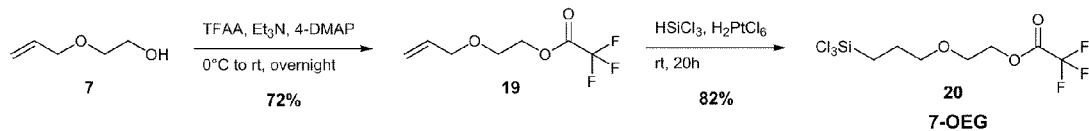
FIG. 7 illustrates Scheme 6, depicting 7-OEG synthesis.

FIG. 7 illustrates Scheme 6, depicting 7-OEG synthesis. 7-OEG (20) was synthesized in two steps from 2-allyloxy-ethanol 7 with a 59% overall yield.

2-allyloxy-ethyl trifluoroacetate (19)

To a stirred solution of 2-allyloxy-ethanol (7) (4.36 mL, 40.0 mmol, 1.0 equiv.), Et$_3$N (11.2 mL, 80.0 mmol, 2.0 equiv.) and 4-DMAP (0.49 g, 4.0 mmol, 0.1 equiv.) in CH$_2$Cl$_2$ (80 mL) was added dropwise trifluoroacetic anhydride (6.74 mL, 48.0 mmol, 1.2 equiv.) at 0° C. After addition, the reaction was allowed to warm to room temperature then stirred overnight. The reaction was then submitted to a CH$_2$Cl$_2$/NH$_4$Cl-saturated aqueous solution extraction. The combined organic layers were dried over anhydrous MgSO$_4$, filtered then evaporated under reduced pressure. Purification was achieved by distillation under reduced pressure and provided 5.76 g (72%) of ester (19) as a colourless oil; bp=72-74° C. (water tap vacuum); $^1$H NMR (300 MHz, CDCl$_3$) δ 5.88 (m, 1H), 5.29 (m, 1H), 5.21 (m, 1H), 4.52 (t, J=4.8 Hz, 2H), 4.03 (m, 2H), 3.76 (t, J=4.8 Hz, 2H); $^{13}$C NMR (75 MHz, CDCl$_3$) δ 157.7 (q, J=42.1 Hz), 134.2, 117.8, 114.7 (q, J=283.9 Hz), 72.4, 67.2, 67.0.

2-(3-trichlorosilyl-propyloxy)-ethyl trifluoroacetate (7-OEG) (20)

In a heavy-walled tube equipped with a magnetic stir bar, ester (19) (3.97 g, 20.0 mmol, 1.0 equiv.) and $H_2PtCl_6.6H_2O$ (104 mg, 0.20 mmol, 1.0 mol. %) were loaded. The tube was transferred into a glovebox and HSiCl$_3$ (4.10 mL, 40.2 mmol, 2.0 equiv.) was added to the solution. The tube was tightly fastened then removed from the glovebox. The resulting solution was stirred at room temperature for 20 h behind a protecting shield. Purification was achieved by Kugelrohr distillation under high vacuum and provided 5.46 g (82%) of 7-OEG (20) as a colourless oil; bp=115-120° C. (0.09 Torr); $^1$H NMR (400 MHz, CDCl$_3$) δ 4.52 (m, 2H), 3.76 (m, 2H), 3.56 (t, J=6.2 Hz, 2H), 1.85 (m, 2H), 1.48 (m, 2H); $^{13}$C NMR (100 MHz, CDCl$_3$) δ 157.7 (q, J=42.3 Hz), 114.7 (q, J=284.1 Hz), 71.8, 67.9, 67.0, 22.8, 21.0.

Biotinthiol Synthesis

Figure 8:
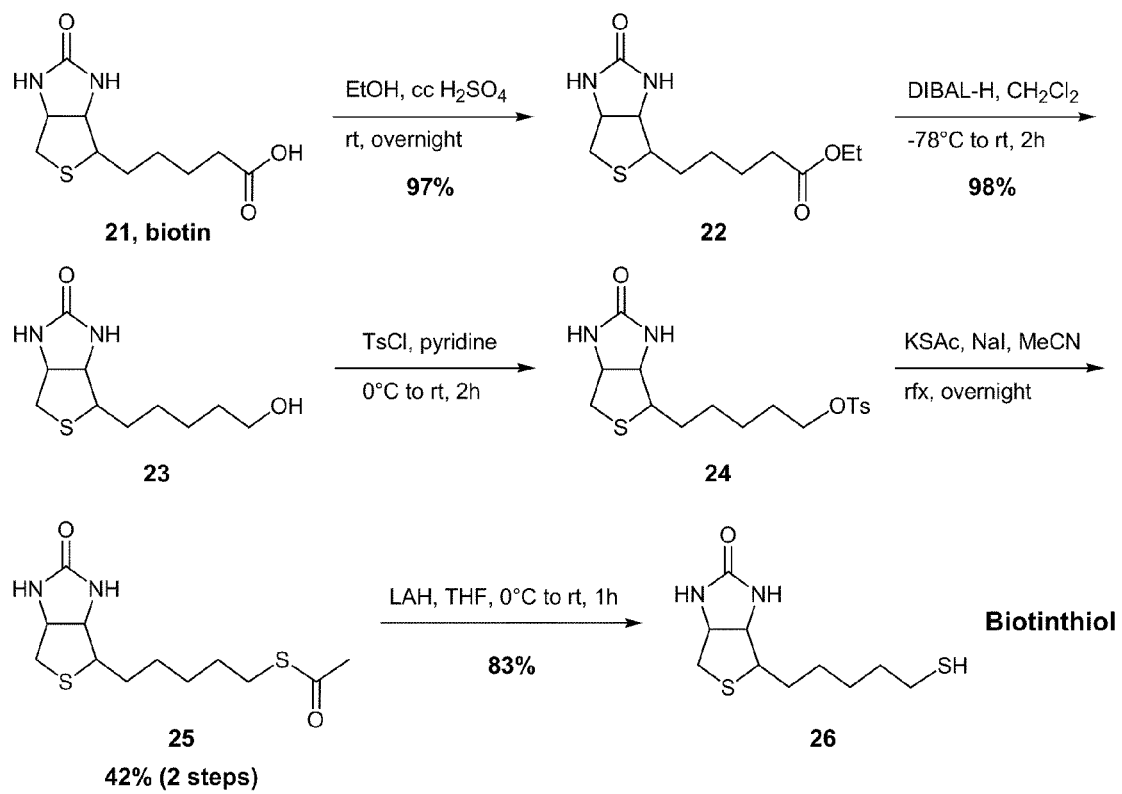
FIG. 8 illustrates Scheme 7, depicting biotinthiol synthesis.

FIG. 8 illustrates Scheme 7, depicting biotinthiol synthesis. Biotinthiol (26) was synthesized in five steps from biotin (21) with a 33% overall yield.

Biotin Methyl Ester (22).[27]

To a stirred solution of biotin (21)(900 mg, 3.65 mmol, 1.0 equiv.) in absolute EtOH (30 mL) were added few drops of concentrated H$_2$SO$_4$ at room temperature. After stirring at room temperature overnight, the reaction was submitted to a CH$_2$Cl$_2$/Na$_2$CO$_3$-aqueous solution extraction. The combined organic layers were dried over anhydrous Na$_2$SO$_4$, filtered then evaporated under reduced pressure to provide 961 mg (97%) of ester 22 as a white solid. Spectroscopic data were consistent with those reported in the literature.[27] $^1$H NMR (400 MHz, CDCl$_3$) δ 5.55 (brs, 1H), 5.17 (brs, 1H), 4.54 (m, 1H), 4.34 (m, 1H), 4.15 (q, J=7.2 Hz, 2H), 3.18 (m, 1H), 2.93 (dd, J=12.8, 4.8 Hz, 1H), 2.75 (d, J=12.8 Hz, 1H), 2.36 (t, J=7.6 Hz, 2H), 1.69 (m, 4H), 1.45 (m, 2H), 1.24 (t, J=7.2 Hz, 3H).

Biotinol 23.[27]

To a stirred solution of biotin methyl ester (22) (961 mg, 3.53 mmol, 1.0 equiv.) in CH$_2$Cl$_2$ (10 mL) was added dropwise DIBAL-H (1.0 M in hexanes, 12.4 mL, 12.4 mmol, 3.5 equiv.) at −78° C. After addition, the reaction was allowed to warm to room temperature then stirred for 2 h. The reaction was then carefully quenched, at −78° C., by dropwise addition of MeOH then H$_2$O. After evaporation of the solvents under reduced pressure, the purification was achieved by Soxhlett extraction (EtOH) and provided 796 mg (98%) of biotinol (23) as a white solid; $^1$H NMR (400 MHz, CD$_3$OD) δ 4.49 (dd, J=7.8, 4.8 Hz, 1H), 4.30 (dd, J=7.8, 4.8 Hz, 1H), 3.55 (t, J=6.6 Hz, 2H), 3.21 (m, 1H), 2.93 (dd, J=12.6, 4.8 Hz, 1H), 2.71 (d, J=12.6 Hz, 1H), 2.16 (s, 1H), 1.74 (m, 1H), 1.57 (m, 3H), 1.45 (m, 4H).

Biotin Tosylate[28] (24) and Biotin Thiocetate (25)

To a stirred solution of biotinol (23) (796 mg, 3.46 mmol, 1.0 equiv.) in pyridine (20 mL) was added tosyl chloride (1.75 g, 9.09 mmol, 2.6 equiv.) at 0° C. After addition, the reaction was allowed to warm to room temperature then stirred for 2 h. The reaction was then submitted to a CH$_2$Cl$_2$/1 M H$_2$SO$_4$ aqueous solution extraction. The combined organic layers were dried over anhydrous Na$_2$SO$_4$, filtered then evaporated under reduced pressure. The residue was rapidly purified by column chromatography on silica gel (EtOAc/MeOH gradient) to provide 697 mg of an off-white solid. The latter was immediately dissolved in anhydrous MeCN (30 mL) then anhydrous NaI (2.65 g, 17.7 mmol) and KSAc (2.06 g, 17.7 mmol) were successively added at room temperature. The reaction was refluxed overnight then submitted to a CH$_2$Cl$_2$/H$_2$O extraction. The combined organic layers were washed with brine, dried over anhydrous Na$_2$SO$_4$, filtered then evaporated under reduced pressure. Purification was achieved by column chromatography on silica gel (CH$_2$Cl$_2$/MeOH gradient) and provided 417 mg (42%, 2 steps) of biotin thioacetate (25) as a beige solid. Spectroscopic data were consistent with those reported in the literature.[29] $^1$H NMR (400 MHz, CDCl$_3$) δ 5.22 (brs, 1H), 4.86 (brs, 1H), 4.55 (m, 1H), 4.34 (m, 1H), 3.17 (m, 1H), 2.94 (dd, J=12.8, 5.2 Hz, 1H), 2.87 (t, J=7.4 Hz, 2H), 2.76 (d, J=12.8 Hz, 1H), 2.36 (s, 3H), 1.64-1.57 (m, 4H), 1.42 (m, 4H).

Biotinthiol (26).[29]

To a stirred solution of biotin thioacetate (25) (410 mg, 1.42 mmol, 1.0 equiv.) in THF (40 mL) was added LAH (95%, 454 mg, 11.36 mmol, 8.0 equiv.) in small portions at 0°

C. After addition, the reaction was allowed to warm to room temperature then stirred for 1 h. The reaction was diluted with EtOAc then carefully quenched with a 1 M HCl aqueous solution. The resulting aqueous layer was extracted with EtOAc. The combined organic layers were washed with brine, dried over anhydrous $Na_2SO_4$, filtered then evaporated under reduced pressure. Purification was achieved by column chromatography on silica gel (EtOAc/MeOH gradient) and provided 291 mg (83%) of biotinthiol (26) as a white solid. Spectroscopic data were consistent with those reported in the literature.29 $^1$H NMR (300 MHz, $CDCl_3$) δ 5.00 (brs, 1H), 4.84 (brs, 1H), 4.55 (m, 1H), 4.35 (m, 1H), 3.20 (m, 1H), 2.95 (dd, J=12.8, 5.2 Hz, 1H), 2.76 (d, J=12.8 Hz, 1H), 2.56 (q, J=7.3 Hz, 2H), 1.76-1.59 (m, 4H), 1.53-1.40 (m, 4H), 1.37 (t, J=7.3 Hz, 1H).

Surface Analyses: Contact Angle Measurement (CAM)

Contact angle measurements (static) were performed in the Department of Chemistry, University of Toronto, Toronto, Canada. Surfaces were analyzed with the KSV contact angle measurement instrument (KSV Instruments Ltd., Linthicum Heights, Md., USA) and ultrapure water as the test liquid. Contact angle values were generated using the CAM101 software.

Surface Analyses: X-Ray Photoelectron Spectroscopy (XPS)

Angle-resolved XPS analysis was performed with a Theta probe ThermoFisher Scientific Instrument (East Grinstead, UK) located at Surface Interface Ontario, University of Toronto, Toronto, ON, Canada. The samples were analyzed with monochromated Al Kα X-rays (elliptical spots of 400 μm along the long axis), with take-off angles of 72.5° and 27.5° relative to the surface. The binding energy scale was calibrated to the main C1s signal at 285 eV. Peak fitting and data analysis were performed using Avantage software provided with the instrument (Table 2).

TABLE 2

Angle-resolved XPS analysis

| Surface | XPS angle | % C1s 285 eV | % F1s 685 eV | % O1s 531 eV | % Si2p 100 eV | % S2p 163 eV |
|---|---|---|---|---|---|---|
| Cleaned quartz disc | 72.5° | 20.1$^a$ | 0.0 | 52.0 | 27.9 | 0.0 |
|  | 27.5° | 6.5$^a$ | 0.0 | 56.4 | 37.1 | 0.0 |
| TTTA/OTS SAM | 72.5° | 26.6 | 2.1 | 48.0 | 23.4 | 0.0 |
|  | 27.5° | 9.0 | 0.9 | 55.6 | 34.5 | 0.0 |
| OEG-TTTA/ 7-OEG SAM | 72.5° | 19.8 | 3.2 | 54.6 | 22.4 | 0.0 |
|  | 27.5° | 6.7 | 1.2 | 56.9 | 35.2 | 0.0 |
| OEG-TUBTS/7- OEG SAM | 72.5° | 31.4 | 6.5 | 44.2 | 16.5 | 1.4 |
|  | 27.5° | 25.7 | 5.8 | 45.7 | 21.3 | 1.5 |

Angle-resolved XPS analysis (72.5° (surface) and 27.5° (bulk)) for cleaned disc as well as TTTA/OTS, OEG-TTTA/7-OEG and OEG-TUBTS/7-OEG mixed SAMs.
$^a$This signal is due to unavoidable surface contamination by adventitious carbon.

Angle-resolved XPS data (along with CAMs in Table 1) were used to determine whether the linker and diluent molecules had deposited from solution onto the quartz slides. Atomic percentages for characteristic elements of the linker/diluent molecules (fluorine and sulfur) along with those for elements (mainly) present in quartz (silicon and oxygen) were calculated and compared before (clean quartz crystal) and after linker/diluent deposition. As expected, clean quartz crystals only showed Si and O as well as unavoidable adventitious carbon. Upon deposition of TTTA/OTS molecules, XPS data were as expected: F signal appeared (and was higher at the surface) and the signals of the underlying buried O and Si decreased. The same was true for the OEG-TTTA/7-OEG system except for the O surface signal, which slightly increased because both OEG-TTTA and 7-OEG molecules possess a non-neglectable amount of O that was reflected in the total amount of O. As expected as well for the OEG-TUBTS/7-OEG system, F and S signals appeared (showing that both molecules deposited) and the signals of the underlying buried O and Si decreased.

In the preceding description, for purposes of explanation, numerous details are set forth in order to provide a thorough understanding of the embodiments of the invention. However, it will be apparent to one skilled in the art that these specific details are not required in order to practice the invention.

The above-described embodiments of the invention are intended to be examples only. Alterations, modifications and variations can be effected to the particular embodiments by those of skill in the art without departing from the scope of the invention, which is defined solely by the claims appended hereto.

All references cited herein are incorporated by reference.

REFERENCES 1. a) Eggins, B. R. In *Chemical Sensors and Biosensors*; John Wiley & Sons Ltd.: Chichester, UK, 2002. b) Collings A. F.; Caruso, F. *Rep. Prog. Phys.* 1997, 60, 1397.
2. Sadik, O. A.; Ngundi, M. M.; Yan, F. *Biotechnol. Bioproc. Eng.* 2000, 5, 407.
3. Del Carlo, M.; Nistor, M.; Campagnone, D.; Mattiasson, B.; Csoregi, E. In *Food Biotechnology (2nd Edition)*; Shetty, K.; Paliyath, G.; Pometto, A.; Levin, R. E. Eds.; Taylor & Francis Group: Boca Raton, Fla., USA, 2006, p 1567.
4. Yu, D.; Blankert, B.; Vire, J.-C.; Kauffmann, J.-M. *Anal. Lett.* 2005, 38, 1687.
5. Gooding, J. J. *Anal. Chim. Acta* 2006, 559, 137.
6. Yang, V. C.; Ngo, T. T. In *Biosensors and Their Applications*; Kluwer Academic/Plenum Publishers: New York, USA, 2000.
7. a) Rusmini, F.; Zhong, Z. Y.; Feijen, J. *Biomacromolecules* 2007, 8, 1775. b) Kim, D. C.; Kang, D. J. *Sensors* 2008, 8, 6605.
8. a) Vericat, C.; Vela, M. E.; Benitez, G. A.; Martin Gago, J. A.; Torrelles, X.; Salvarezza, R. C. *J. Phys.: Condens. Matter* 2006, 18, R867. b) Shenhar, R.; Norsten, T. B.; Rotello, V. M. In *Introduction to Nanoscale Science and Technology*; Di Ventra, M.; Evoy, S.; Heflin, J. R. Eds.: Springer: New York, USA, 2004, p 41. c) Ulman, A. *Chem. Rev.* 1996, 96, 1533.
9. a) Camarero, J. A. *Biophys. Rev. Lett.* 2006, 1, 1. b) Lee, Y. W.; Reed-Mundell, J.; Zull, J. E.; Sukenik, C. N. *Langmuir* 1993, 9, 3009.
10. Azioune, A.; Pireaux, J.-J.; Houssiau, L. *Appl. Surf. Sci.* 2004, 231-2, 402.
11. a) Chrisey, L. A.; Lee, G. U.; O'Ferrall, C. E. *Nucleic Acids Res.* 1996, 24, 3031. b) Saoud, M.; Blaszykowski, C.; Ballantyne, S. M.; Thompson, M. *Analyst* 2009, 134, 835.
12. a) Wink, T.; van Zuilen, S. J.; Bult, A.; van Bennekom, W. P. *Analyst* 1997, 122, 43R. b) Chaki, N. K.; Vijayamohanan, K. *Biosens. Bioelectron.* 2002, 17, 1. c) Luderer, F.; Walschus, U. *Top. Curr. Chem.* 2005, 260, 37. d) Ferretti, S.; Paynter, S.; Russell, D. A.; Sapsford, K. E.; Richardson, D. J. *Trends Anal. Chem.* 2000, 19, 530. e) Liedberg, B.; Cooper, J. M. In *Immobilized Biomolecules in Analysis: A practical Approach*; Cass, T.; Ligler, F. S. Eds.: Oxford University Press, Oxford, UK, 1998, p 55.
13. a) Guilbault, G. G.; Jordan, J. M.; Scheide, E. *CRC Crit. Rev. Anal. Chem.* 1988, 19, 1. b) Deakin, M. R.; Buttry, D. A. *Anal. Chem.* 1989, 61, 1147A.

14. a) Sheikh, S.; Blaszykowski, C.; Thompson, M. *Anal. Lett.* 2008, 41, 2525. b) Gronewold, T. M. A. *Anal. Chim. Acta* 2007, 603, 119.
15. Selected reviews: a) Rickert, J.; Gopel, W.; Hayward, G. L.; Čaviá, B. A.; Thompson, M. In *Sensors Update (Volume 5)*; Baltes, H.; Gopel, W.; Hesse, J. Eds.; Wiley-VCH: Weinheim, Germany, 1999, p 105. b) Čaviá, B. A.; Hayward, G. L.; Thompson, M. *Analyst* 1999, 124, 1405. c) Cooper, M. A.; Singleton, V. T. *J. Mol. Recognit.* 2007, 20, 154. d) Länge, K.; Rapp, B. E.; Rapp, M. *Anal. Bioanal. Chem.* 2008, 391, 1509.
16. a) Thompson, M.; Ballantyne, S. M.; Cheran, L.-E.; Stevenson, A. C.; Lowe, C. R. *Analyst* 2003, 128, 1048. b) Thompson, M.; Ballantyne, S. M. *Electromagnetic piezoelectric acoustic sensor* 2007, U.S. Pat. No. 7,207,222.
17. Ballantyne, S. M.; Thompson, M. *Analyst* 2004, 129, 219.
18. a) McGovern, M. E.; Thompson, M. *Anal. Commun.* 1998, 35, 391. b) McGovern, M. E.; Thompson, M. *Can. J. Chem.* 1999, 77, 1678.
19. Savage, M. D.; Mattson, G.; Desai, S.; Nielander, G. W.; Morgensen, S.; Conklin, E. J. In *Avidin-Biotin Chemistry: A Handbook*; Pierce Chemical Company: Rockford, Ill., USA, 1992.
20. Wasserman, S. R.; Tao, Y.-T.; Whitesides, G. M. *Langmuir* 1989, 5, 1074.
21. Fryxell, G. E.; Rieke, P. C.; Wood, L. L.; Engelhard, M. H.; Williford, R. E.; Graff, G. L.; Campbell, A. A.; Wiacek, R. J.; Lee, L.; Halverson, A. *Langmuir* 1996, 12, 5064.
22. Lee, J. W.; Sim, S. J.; Cho, S. M.; Lee, J. *Biosens. Bioelectron.* 2005, 20, 1422.
23. a) Anderson, A. S.; Dattelbaum, A. M.; Mukundan, H.; Price, D. N.; Grace, W. K.; Swanson, B. I. In *Proceedings of SPIE, Frontiers in Pathogen Detection: From Nanosensors to Systems (Films and Substrates)*; Fauchet, M. Ed.; 2009, 7167, 7167Q1. See also: b) Zheng, J.; Li, L.; Tsao, H.-K.; Sheng, Y.-J.; Chen, S.; Jiang, S.; *Biophys. J.* 2005, 89, 158.
24. a) Ostuni, E.; Chapman, R. G.; Holmlin, R. E.; Takayama, S.; Whitesides, G. M. *Langmuir* 2001, 17, 5605. b) Ngadi, N.; Abrahamson, J.; Fee, C.; Morison, K. *WASET: Engineering and Technology (proceedings)* 2009, 49, 144. c) Snellings, G. M. B. F.; Vansteenkiste, S. O.; Corneillie, S. I.; Davies, M. C.; Schacht, E. H. *Adv. Mater.* 2000, 12, 1959. d) Ostuni, E.; Chapman, R. G.; Liang, M. N.; Meluleni, G.; Pier, G.; Ingber, D. E.; Whitesides, G. M. *Langmuir* 2001, 17, 6336. e) Xia, N.; Hu, Y.; Grainger, D. W.; Castner, D. G. *Langmuir* 2002, 18, 3255. f) Jeon, S. I.; Lee, J. H.; Andrade, J. D.; De Gennes, P.-G. *J. Colloid Interface Sci.* 1991, 142, 149.
25. a) Parsons, T. F.; Buckman, J. D.; Pearson, D. E.; Field, L. *J. Org. Chem.* 1965, 30, 1923. b) Kice, J. L.; Rogers, T. E. *J. Am. Chem. Soc.* 1974, 96, 8015.
26. a) Delgado, M.; Martin, J. D. *J. Org. Chem.* 1999, 64, 4798. b) Doyle, M. P.; Hu, W. *J. Org. Chem.* 2000, 65, 8839.
27. Corona, C.; Bryant, B. K.; Arterburn, J. B. *Org. Lett.* 2006, 8, 1883.
28. DeLaLuz, P. J.; Golinski, M.; Watt, D. S.; Vanaman, T. C. *Bioconjugate Chem.* 1995, 6, 558.
29. Galonić, D.; Ide, N. D.; van der Donk, W. A.; Gin, D. Y. *J. Am. Chem. Soc.* 2005, 127, 7359.

What is claimed is:

1. An acoustic wave biosensor comprising a surface of a mixed self-assembling monolayer for receiving a biomolecule;
   wherein the mixed self-assembling monolayer comprises a 2,2,2-trifluoroethyl-13-trichlorosilyl-tridecanoate (TTTA); OEGylated TTTA (OEG-TTTA); or S-(2-(2-(2-(3-trichlorosilyl-propyloxy)-ethoxy)-ethoxy)-ethyl)-benzenethiosulfonate (OEG-TUBTS) linker.

2. The acoustic wave biosensor of claim 1, wherein the mixed self-assembling monolayer comprises a linker/diluent system wherein the diluent comprises octadecyltrichlorosilane (OTS) or 2-(3-trichlorosilyl-propyloxy)-ethyl-trifluoroacetate (7-OEG).

3. The biosensor of claim 2 wherein the linker/diluent system comprises TTTA/OTS, OEG-TTTA/7-OEG, or OEG-TUBTS/7-OEG.

4. The biosensor of claim 1 wherein the surface is functionalized for target analyte detection with the electromagnetic piezoelectric acoustic sensor (EMPAS).

5. The biosensor of claim 4 wherein the mixed self-assembling monolayer on the surface is functionalized with a biotin derivative.

6. The biosensor of claim 5 wherein the biotin derivative comprises biotinthiol.

7. A linker for attaching a functionalizing entity to the surface of a biosensor comprising an oligoethylene glycol linker, for decreasing the amount of non-specific adsorption, wherein the linker comprises OEG-TTTA or OEG-TUBTS.

8. The biosensor of claim 2 wherein the surface comprises a piezoelectric quartz crystal surface with a mixed self-assembling monolayer thereon for electromagnetic piezoelectric acoustic sensor (EMPAS) technology.

9. The biosensor of claim 2 wherein the surface is functionalized for target analyte detection with the electromagnetic piezoelectric acoustic sensor (EMPAS).

10. The biosensor of claim 9 wherein the mixed self-assembling monolayer on the surface is functionalized with a biotin derivative.

11. The biosensor of claim 10 wherein the biotin derivative comprises biotinthiol.

12. The biosensor of claim 1 wherein the surface comprises a piezoelectric quartz crystal surface with a mixed self-assembling monolayer thereon for electromagnetic piezoelectric acoustic sensor (EMPAS) technology.

13. An acoustic wave biosensor comprising a surface of a mixed self-assembling monolayer for receiving a biomolecule;
    wherein the mixed self-assembling monolayer comprises a linker/diluent system wherein the diluent comprises 2-(3-trichlorosilyl-propyloxy)-ethyl-trifluoroacetate (7-OEG).

14. The acoustic wave biosensor of claim 13 wherein the linker/diluent system comprises OEG-TTTA/7-OEG or OEG-TUBTS/7-OEG.

15. The biosensor of claim 13 wherein the surface comprises a piezoelectric quartz crystal surface with a mixed self-assembling monolayer thereon for electromagnetic piezoelectric acoustic sensor (EMPAS) technology.

16. The biosensor of claim 13 wherein the surface is functionalized for target analyte detection with the electromagnetic piezoelectric acoustic sensor (EMPAS).

17. The biosensor of claim 16 wherein the mixed self-assembling monolayer on the surface is functionalized with a biotin derivative.

18. The biosensor of claim 17 wherein the biotin derivative comprises biotinthiol.

* * * * *